(12) United States Patent
Epstein et al.

(10) Patent No.: US 10,485,550 B2
(45) Date of Patent: Nov. 26, 2019

(54) OPHTHALMIC DRUG DELIVERY DEVICE AND METHODS OF USE

(71) Applicants: David L. Epstein, Bahama, NC (US); Stuart McKinnon, Durham, NC (US); Molly Walsh, Chapel Hill, NC (US)

(72) Inventors: David L. Epstein, Bahama, NC (US); Stuart McKinnon, Durham, NC (US); Molly Walsh, Chapel Hill, NC (US)

(73) Assignee: DUKE UNIVERSITY, Durham, NC (US)

( * ) Notice: Subject to any disclaimer, the term of this patent is extended or adjusted under 35 U.S.C. 154(b) by 674 days.

(21) Appl. No.: 14/388,689

(22) PCT Filed: Mar. 15, 2013

(86) PCT No.: PCT/US2013/031870
§ 371 (c)(1),
(2) Date: Sep. 26, 2014

(87) PCT Pub. No.: WO2013/148301
PCT Pub. Date: Oct. 3, 2013

(65) Prior Publication Data
US 2015/0057689 A1    Feb. 26, 2015

Related U.S. Application Data

(60) Provisional application No. 61/616,039, filed on Mar. 27, 2012.

(51) Int. Cl.
*A61B 17/12* (2006.01)
*A61F 9/00* (2006.01)
(Continued)

(52) U.S. Cl.
CPC ............ *A61B 17/12* (2013.01); *A61F 9/0017* (2013.01); *A61K 9/0048* (2013.01); *A61K 9/14* (2013.01);
(Continued)

(58) Field of Classification Search
CPC ........ A61K 9/0048; A61K 9/14; A61K 31/00; A61K 31/192; A61K 31/198;
(Continued)

(56) References Cited

U.S. PATENT DOCUMENTS 4,558,698 A    12/1985    O'Dell
5,795,103 A    8/1998    Schwartz et al.
(Continued)

FOREIGN PATENT DOCUMENTS

CN    201073464    6/2008
WO    1999017691    4/1999
(Continued)

OTHER PUBLICATIONS

Dr. Florian Rufer, White-to-White Corneal Diameter: Normal Values in Healthy Humans Obtained With the Orbscan II Topography System, Apr. 2005, Cornea, vol. 24, Issue 3, pp. 259-261.*
(Continued)

*Primary Examiner* — George J Ulsh
(74) *Attorney, Agent, or Firm* — McDonnell Boehnen Hulbert & Berghoff LLP

(57) ABSTRACT

The present disclosure provides an elastomeric material for the delivery of an ophthalmic agent to the eye of a subject and methods of using such material.

18 Claims, 11 Drawing Sheets

(51) Int. Cl.
*A61K 9/00* (2006.01)
*A61K 9/14* (2006.01)
*A61K 31/00* (2006.01)
*A61K 31/192* (2006.01)
*A61K 31/198* (2006.01)
*A61K 31/728* (2006.01)
*A61L 31/06* (2006.01)
*A61F 9/007* (2006.01)

(52) U.S. Cl.
CPC ............ *A61K 31/00* (2013.01); *A61K 31/192* (2013.01); *A61K 31/198* (2013.01); *A61K 31/728* (2013.01); *A61L 31/06* (2013.01); *A61F 9/007* (2013.01)

(58) Field of Classification Search
CPC ........ A61F 9/0017; A61F 9/007; A61F 2/147; A61L 31/06; A61B 17/12
USPC ........................................................ 606/158
See application file for complete search history.

(56) References Cited

U.S. PATENT DOCUMENTS

| 7,273,475 | B2 | 9/2007 | Tu et al. |
| 2003/0033015 | A1 | 2/2003 | Zhou et al. |
| 2005/0149184 | A1 | 7/2005 | Bogaert |
| 2005/0182013 | A1 | 8/2005 | Wolff et al. |
| 2006/0003964 | A1* | 1/2006 | Shah .................... A61K 31/716 514/54 |
| 2006/0047263 | A1* | 3/2006 | Tu ....................... A61F 9/00781 604/521 |
| 2006/0253110 | A1* | 11/2006 | Rosen ..................... A61F 9/008 606/4 |
| 2007/0123814 | A1 | 5/2007 | Roy |
| 2007/0282405 | A1 | 12/2007 | Wong, Jr. et al. |
| 2008/0177383 | A1* | 7/2008 | Shahinpoor ............. A61F 2/147 623/5.12 |
| 2010/0318034 | A1 | 12/2010 | Goncalves |

FOREIGN PATENT DOCUMENTS

| WO | 2003009774 A2 | 2/2003 |
| WO | 2010141726 | 12/2010 |
| WO | WO2010141729 | 12/2010 |

OTHER PUBLICATIONS

International Search Report dated Jul. 9, 2013 of PCT/US2013/031870 filed Mar. 15, 2013.

Quigley et al., "Lack of neuroprotection against experimental glaucoma in c-Jun N-terminal kinase 3 knockout mice", Exp Eye Res., 92(4):299-305. (Apr. 2011).

Shafaa, Medhat et al. "The extended ocular hypotensive effect of positive liposomal cholesterol bound timolol maleate in glaucomatous rabbits," Biopharm. Drug Dispos. 32: 507-517 (2011).

* cited by examiner

OPHTHALMIC DRUG DELIVERY DEVICE AND METHODS OF USE

CROSS-REFERENCES TO RELATED APPLICATIONS

This application is a U.S. national phase phase of International Application No. PCT/US 2013/031870,filed Mar. 15,2013,claims benefit of U.S. Provisional Application Ser. No. 61/616,039 ,filed Mar. 27, 2012 , which is incorporated by reference herein in its entirety.

STATEMENT REGARDING FEDERALLY SPONSORED RESEARCH

This invention was produced in part using funds from the Federal Government under NIH/NEI Grant No.: 5RO1EY001894-33 entitled "Metabolism of the Trabecular Meshwork" and NIH/NEI Grant No.: 5K08EY019726-02 entitled "NEI Mentored Clinical Scientist Development Award." Accordingly, the Federal Government has certain rights to this invention.

BACKGROUND

Field of the Disclosure

The disclosure relates to methods and materials for the delivery of ophthalmic agents to the eye of a subject.

Description of Related Art

Glaucoma is characterized by intraocular pressure resulting at least in part from a diminished outflow of aqueous humor through the trabecular meshwork. Many current therapies for the treatment of glaucoma involve the topical administration of medicaments to the eye via eye drops. However, topical administration has many downsides, since many of the medicaments are poor at penetrating the cornea and/or may also have un desired side effects, such as external irritation and redness. Moreover, there are several documented studies that show patients have a great deal of difficulty administering topical medicaments (e.g., eye drops), and consequently there is poor compliance and adherence by patients with topical glaucoma medicaments.

There is evidence suggesting both patients and medical staff would prefer and that ocular injection for glaucoma that could be given 3-4 times a year over the current topical administration.

SUMMARY OF THE INVENTION

The present disclosure addresses the unmet need for treatment with ophthalmic agents by providing an ophthalmic drug delivery device for the direct administration of ophthalmic agents into the eye of the subject.

One aspect of present disclosure provides an elastomeric material for the occlusion of venous blood flow within the episcleral vein of an eye of a subject comprising, consisting of, or consisting essentially of:
  (a) a central opening with an inner diameter therein; and
  (b) an outer diameter of at least 1 mm,
wherein when the elastomeric material is placed upon the eye, the inner diameter portion is stretched to fit around the equator of the eye and, upon contraction, the venous blood flow within the episcleral vein of the eye is occluded.

In one embodiment, the elastomeric material comprises a shape selected from the group consisting of circular, oval, ellipse, rectangular, and square.

In another embodiment, the elastomeric material comprises an outer diameter between about 2 mm to about 40 mm.

In other embodiments, the inner diameter of the flexible material is about 2 mm to about 20 mm.

In another embodiment, the elastomeric material comprises a silastic material.

Another aspect of the present disclosure provides a method of increasing aqueous humor outflow in the eye of a subject suffering from glaucoma comprising, consisting of, or consisting essentially of:
  (a) placing the elastomeric material according to the present disclosure around the equator of the eye thereby occluding venous blood flow within the episcleral vein;
  (b) administering via the episcleral vein a therapeutically effective amount of an ophthalmic agent; and
  (c) removing the elastomeric material from the eye.

In yet another aspect, the present disclosure provides a method of delivering an ophthalmic agent to the aqueous outflow system comprising, consisting of, or consisting essentially of:
  (a) placing the elastomeric material according to the present disclosure around the equator of the eye thereby occluding venous blood flow within the episcleral vein;
  (b) administering via the episcleral vein a therapeutically effective amount of the ophthalmic agent; and
  (c) removing the elastomeric material from the eye.

Another aspect of the present disclosure provides a method of delivering an ophthalmic agent to the anterior chamber of the eye comprising, consisting of, or consisting essentially of:
  (a) placing the elastomeric material according to the present disclosure around the equator of the eye thereby occluding venous blood flow within the episcleral vein;
  (b) administering via the episcleral vein a therapeutically effective amount of the ophthalmic agent; and
  (c) removing the elastomeric material from the eye.

Another aspect of the present disclosure provides a method of inducing a glaucoma-like condition in a subject comprising, consisting of, or consisting essentially of:
  (a) placing the elastomeric material according to the present disclosure around the equator of the eye thereby occluding venous blood flow within the episcleral vein;
  (b) administering via the episcleral vein an effective amount of an ophthalmic agent and viscoelastic agent;
  (c) removing the elastomeric material from the eye.

In one embodiment, the ophthalmic agent comprises outflow increasing agents, steroids, alpha receptor agonists, beta receptor antagonists, carbonic anhydrase inhibitors, adrenergic agents, physiologically active peptides and/or proteins, antineoplastic agents, antibiotics, analgesics, anti-inflammatory agents, muscle relaxants, anti-epileptics, anti-ulcerative agents, anti-allergic agents, cardiotonics, anti-arrhythmic agents, vasodilators, antihypertensive agents, anti-diabetic agents, anti-hyperlipidemics, anticoagulants, hemolytic agents, antituberculous agents, hormones, narcotic antagonists, osteoclastic suppressants, osteogenic promoters, angiogenesis suppressors, antibacterials, non-steroidal anti-inflammatory drugs (NSAIDs), glucocorticoids or other anti-inflammatory corticosteroids, alkaloid analgesics, such as opioid analgesics, antivirals, such as nucleoside antivirals or a non-nucleoside antivirals, anti-benign prostatic hypertrophy (BPH) agents, anti-fungal compounds, antiproliferative compounds, anti-glaucoma compounds, immunomodulatory compounds, cell transport/mobility impeding agents, cytokines pegylated agents, alpha-blockers, anti-androgens, anti-cholinergic agents, purinergic agents, dopaminergic agents, local anesthetics, vanilloids, nitrous oxide inhibitors, anti-apoptotic agents, macrophage activation inhibitors, antimetabolites, neuroprotectants, calcium channel blockers, gamma-aminobutyric acid (GABA) antagonists, alpha agonists, anti-psychotic agents, tyrosine kinase inhibitors, nucleoside compounds, and nucleotide compounds, and analogs, derivatives, pharmaceutically acceptable salts, esters, prodrugs, codrugs, and protected forms thereof, and combinations thereof.

In certain embodiments, outflow increasing agent comprises ethacrynic acid or any analogs or derivatives thereof.

In other embodiments, the ophthalmic agent is administered with a viscoelastic agent. In certain embodiments, the viscoelastic agent is selected from the group consisting of Healon® (Abbott Laboratories Inc., Abbott Park, Ill., USA), Healon®OVD, Healon5®OVD, HealonGV®, ProVisc® (Alcon Laboratories, Inc., Fort Worth, Tex., USA), and combinations thereof. In other embodiments, the ratio of ophthalmic agent to viscoelastic agent is 3:1.

Another aspect provides for all that is described and illustrated herein.

BRIEF DESCRIPTION OF THE DRAWINGS

The foregoing aspects and other features of the invention are explained in the following description, taken in connection with the accompanying drawings, wherein.

DETAILED DESCRIPTION OF THE INVENTION

Figure 1:
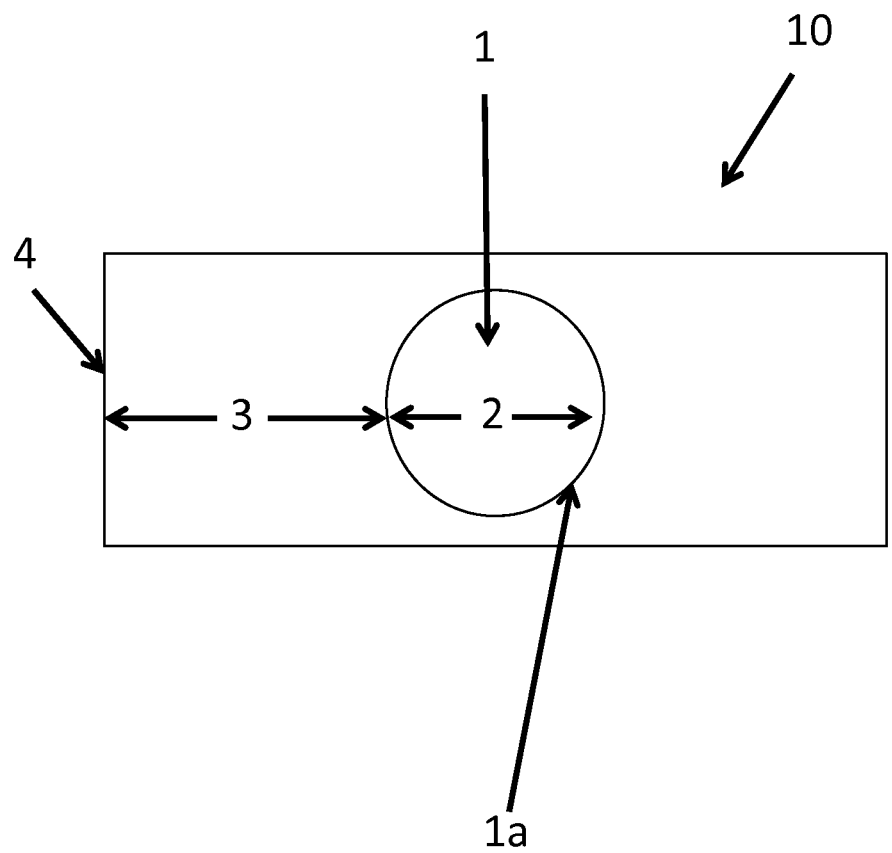
FIG. 1 is a plane view and sectional view of one embodiment of the elastomeric material of the present disclosure.

For the purposes of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Definitions

Unless otherwise defined, all technical terms used herein have the same meaning as commonly understood by one of ordinary skill in the art to which this disclosure belongs. Certain terms are discussed herein to provide additional guidance to the practitioner in describing the devices, methods, and the like, of embodiments of the disclosure, and how to make or use them. It will be appreciated that the same thing can be said in more than one way. Consequently, alternative language and synonyms can be used for any one or more of the terms discussed herein. No significance is to be placed upon whether or not a term is elaborated or discussed herein. Some synonyms or substitutable methods, materials and the like are provided. Recital of one or a few synonyms or equivalents does not exclude use of other synonyms or equivalents, unless it is explicitly stated.

Articles "a" and "an" are used herein to refer to one or to more than one (i.e. at least one) of the grammatical object of the article. By way of example, "an element" means at least one element and can include more than one element.

As used herein, the term "patient" or "subject" is intended to include human and non-human animals. Exemplary human subjects include a human patient having an ocular disorder, e.g., glaucoma. The term "non-human animals" includes all vertebrates, e.g., non-mammals (such as chickens, amphibians, reptiles) and mammals, such as non-human primates, domesticated and/or agriculturally useful animals (such as sheep, dogs, cats, cows, pigs, etc.), and rodents (such as mice, rats, hamsters, guinea pigs, etc.).

As used herein, the term "therapeutically effective" or "effective amount" refers to a dosage of a compound (e.g., an ophthalmic agent, an outflow increasing agent, etc.) effective for eliciting a desired effect. This term as used herein may also refer to an amount effective at bringing about a desired in vivo effect in an animal, mammal, or human, such as reducing intraocular pressure, inflammation, and the like. The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

The term "administration" or "administering," as used herein, refers to providing, contacting, and/or delivery of a compound, such as an ophthalmic agent or outflow increasing agent, and the like by any appropriate route to achieve the desired effect. These compounds may be administered to a subject in numerous ways including, but not limited to, oral, sublingual, parenteral (e.g., intravenous, subcutaneous, intracutaneous, intramuscular, intraarticular, intraarterial, intrasynovial, intrasternal, intrathecal, intralesional or intracranial injection), transdermal, topical, buccal, rectal, vaginal, nasal, ophthalmic, via inhalation, and implants. In some embodiments, the compounds are administered parenterally. In certain embodiments, the compounds are administered intravenously.

"Pharmaceutically acceptable" means approved or approvable by a regulatory agency of the Federal or state government or listed in the U.S. Pharmacopoeia or other generally recognized pharmacopoeia for use in animals, and more particularly in humans. It can be material which is not biologically or otherwise undesirable, i.e., the material can be administered to an individual without causing any undesirable biological effects or interacting in a deleterious manner with any of the components of the composition in which it is contained.

The term "pharmaceutically acceptable salt" of a compound means a salt that is pharmaceutically acceptable and that possesses the desired pharmacological activity of the parent compound. Such salts include, for example, acid addition salts and base addition salts.

The term "agonist" refers to a compound that can combine with a receptor to produce or increase a molecular and cellular activity. An agonist may be a ligand that directly binds to the receptor. Alternatively, an agonist may combine with a receptor indirectly by, for example, (a) forming a complex with another molecule or protein that directly binds to the receptor, or (b) otherwise results in the modification of another compound so that the other compound directly binds to the receptor.

The term "antagonist" refers to a compound that can combine with a receptor to reduce or inhibit a molecular and cellular activity. An antagonist may be a ligand that directly binds to the receptor. Alternatively, an antagonist may combine with a receptor indirectly by, for example, (a) forming a complex with another molecule or protein that directly binds to the receptor, or (b) otherwise results in the modification of another compound so that the other compound directly binds to the receptor.

As used herein, terms including, but not limited to "peptide," or "protein," "or any other term used to refer to a chain or chains of two or more amino acids. The term further includes peptides which have undergone post-translational modifications, for example, glycosylation, acetylation, phosphorylation, amidation, derivatization by known protecting/blocking groups, proteolytic cleavage, or modification by non-naturally occurring amino acids.

The present disclosure is explained in the following by referring to preferable embodiments.

The elastomeric material of the present disclosure provides for the occlusion of venous blood flow within the episcleral vein of an eye of a subject and is mainly characterized in that it has a central opening with an inner diameter therein, an outer diameter of at least 1 mm, wherein when the elastomeric material is placed upon the eye, the inner diameter portion is stretched to fit around the equator of the eye and, upon contraction, the venous blood flow within the episcleral vein of the eye is occluded.

Shape and Size of Elastomeric Material

FIG. 1 is a plane view and section view of one embodiment of the elastomeric material of the present disclosure. The elastomeric material of the present disclosure, shown as 10 in the figure, comprises, consists of, or consists essentially of a sheet of elastomeric material that has a central opening 1 with an inner diameter 2, and an outer diameter 3.

The planar shape (i.e., outline of the outer circumference of the elastomeric material) of the material is not particularly limited and can take the form of many different shapes, including but not limited to, circular, oval, ellipse, rectangular, square and the like. In certain embodiments, the shape of the material is square. In other embodiments, the shape is substantially circular. As used herein, the term "substantially circular" is not limited to an about true circle, but includes ellipse and elongated ellipse. In certain embodiments, the shape of the material is a true circle.

The size of the elastomeric material of the present disclosure in also not particularly limited as long as it can be placed over the eye and easily manipulated by the caregiver (i.e., easily positioned on the eye, stretched, etc.). In certain embodiments, the material comprises a shape generally as shown in FIG. 1. In such embodiments, the outer diameter 3 is about 1 mm to about 20 mm, 2 mm to about 20 mm, 3 mm to about 20 mm, 4 mm to about 20 mm, 5 mm to about 20 mm, 6 mm to about 20 mm, 7 mm to about 20 mm, 8 mm to about 20 mm, 9 mm to about 20 mm, 10 mm to about 20 mm, 11 mm to about 20 mm, 12 mm to about 20 mm, 13 mm to about 20 mm, 14 mm to about 20 mm, 15 mm to about 20 mm, 16 mm to about 20 mm, 17 mm to about 20 mm, 18 mm to about 20 mm, 19 mm to about 20 mm, about 1 mm to about 30 mm, 1 mm to about 40 mm, 5 mm to about 30 mm, 5 mm to about 40 mm, 8 mm to about 30 mm, 8 mm to about 40 mm, 10 mm to about 30 mm, 10 mm to about 40 mm, 15 mm to about 30 mm, 15 mm to about 40 mm, 20 mm to about 30 mm, 20 mm to about 40 mm, 22 mm to about 30 mm, 22 mm to about 40 mm, 25 mm to about 30 mm, 25 mm to about 40 mm, 30 mm to about 40 mm, and 35 mm to about 40 mm, to facilitate the caregiver in grasping the material in order to stretch the central opening 1. In other embodiments, the inner diameter 2 is of sufficient size that when stretched, it is able to fit around the equator of the eye, and when released to its relaxed state, constricts such that the venous blood flow within the episcleral vein is occluded. In certain embodiments, the inner diameter 2 is about 1 mm to about 10 mm, 2 mm to about 10 mm, 3 mm to about 10 mm, 4 mm to about 10 mm, 5 mm to about 10 mm, 6 mm to about 10 mm, 7 mm to about 10 mm, 8 mm to about 10 mm, 9 mm to about 10 mm, 1 mm to about 20 mm, 2 mm to about 20 mm, 3 mm to about 20 mm, 4 mm to about 20 mm, 5 mm to about 20 mm, 6 mm to about 20 mm, 7 mm to about 20 mm, 8 mm to about 20 mm, 9 mm to about 20 mm, 10 mm to about 20 mm, 11 mm to about 20 mm, 12 mm to about 20 mm, 13 mm to about 20 mm, 14 mm to about 20 mm, 15 mm to about 20 mm, 16 mm to about 20 mm, 17 mm to about 20 mm, 18 mm to about 20 mm, 19 mm to about 20 mm.

Herein, the inner edge portion 1a refers to the portion of the elastic material that runs along the inner circumference of the central opening. The inner edge portion 1a comprises a thickness of generally no more than about 0.3 mm. In certain embodiments, the inner edge portion comprises a thickness within the range of 0.05-0.3 mm, 0.1-0.3 mm, or 0.13-0.23 mm. Similarly, the outer edge portion 4 is generally set to not be more than about 0.3 mm. In some embodiments, the outer edge portion 4 is within the range of 0.05-0.3 mm, 0.15-0.3 mm, and 0.17-0.3 mm. Both the inner edge portion and the outer edge portion may be formed to have a substantially uniform thickness. In some embodiments, the inner edge portion may be formed to have an decreasing thickness from the inner edge to the outer edge portion, such that the inner edge portion is thicker than the outer edge portion. The thickness of the outer diameter portion 3a is generally set to be not more than about 0.4 mm. In certain embodiments, the outer diameter portion 3a comprises a thickness within the range of about 0.08-0.4 mm, 0.2-0.4 mm, and 0.33-0.38 mm. In some embodiments, the outer diameter portion comprises a thickness of greater than 0.03 mm or more than both the maximum thickness of the outer edge portion and the inner edge portion.

Composition of Elastic Material

Figure 2:
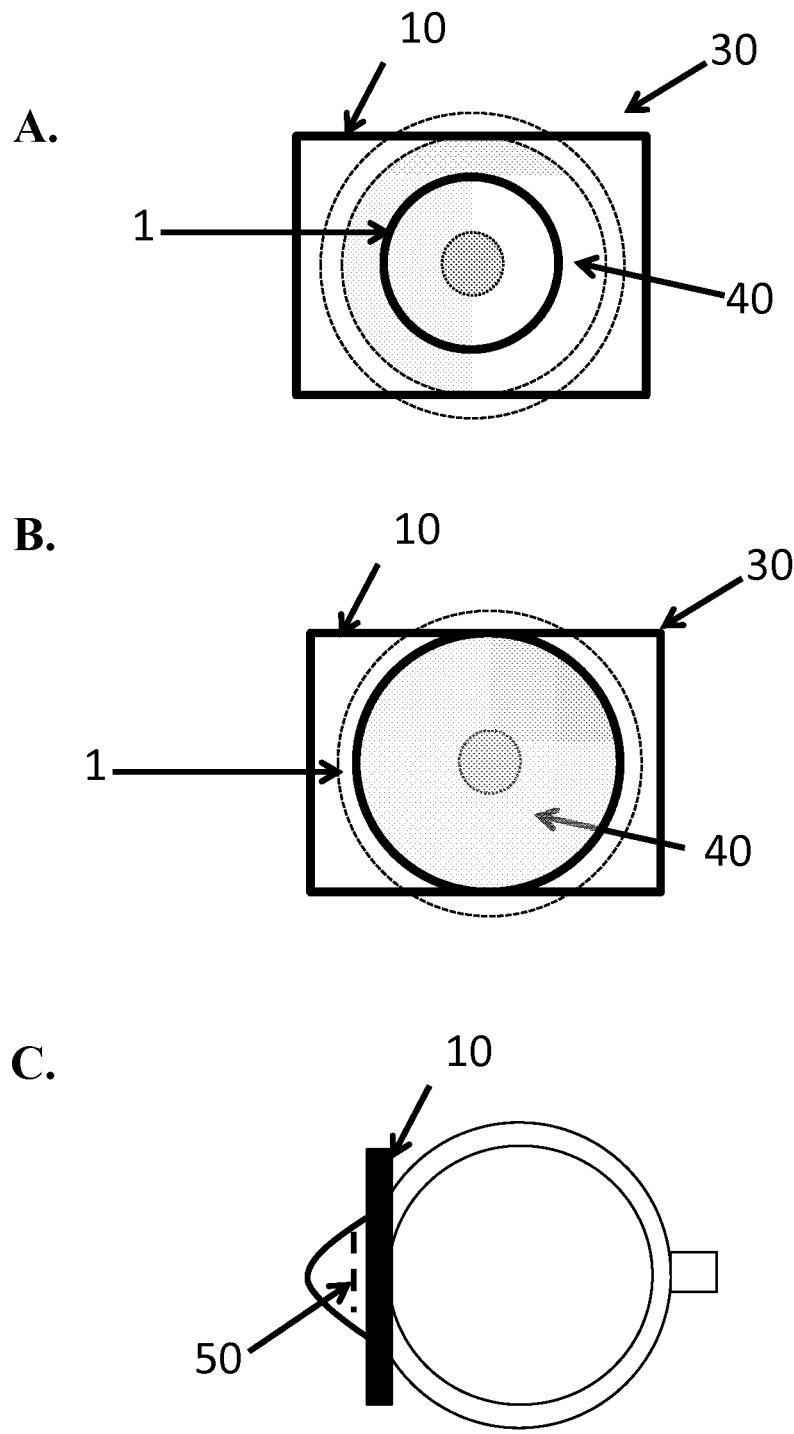
FIG. 2a shows the initial placement of the elastomeric material onto an eye in accordance with one embodiment of the present disclosure.
FIG. 2b shows the stretching of the elastomeric material onto the eye in accordance with one embodiment of the present disclosure.
FIG. 2c provides a side view showing the state of applying the elastomeric material to the eye of a subject in accordance with one embodiment of the present disclosure.

The elastic material of the present disclosure comprises an elastic-like material which enables the extension of the central opening by between about 1% and 50%, 5% and 40% and 10% and 40%, where the elastic-like material has a bias to return to its original shape. In practice, and as shown in FIG. 2a, the material 10 is placed on the eye 30 such that the central opening is positioned over the equator 40 of the eye. The material 20 is then stretched such that the central opening 1 is larger than the equator of the eye (FIG. 2b). The material 20 is then relaxed, wherein in its relaxed state, the central opening is contracted around the equator 40 of the eye that the venous blood flow within the episcleral vein 50 is occluded (FIG. 2c). This occlusion causes the vein to become swollen, allowing for easy access and visualization of the episcleral vein by the caregiver. Suitable elastic-like materials are those which are preferably biologically inert and may include, but are not limited to elastomer (elastic polymer) materials such as polyurethane, polyethylene, silicone elastics (e.g., Silastic™ silicone materials), a thermoplastic elastomer such as Styrene-ethylene/butylene-styrene (SEBS), Styrene-ethylene/propylene-styrene (SEPS) ethylene-propylene copolymer/polypropylene (EPDM-PP), polyether block amides (PEBAX), polyurethane or further a vulcanizable elastomers such as silicone rubber, latex, polybutadiene, a fluorinated elastomer, polychloroprene, polyisoprene, materials and the like. In certain embodiments, the elastomeric material comprises Silastic™ silicone.

Methods of Use

The elastomeric material described herein allows for the ocular delivery of ophthalmic agents to the Schlemm's Canal and the trabecular meshwork outflow of a subject's eye, greatly enhancing the effect of these agents on the eye. For example, delivery of certain glaucoma agents directly into the Schlemm's Canal and trabecular meshwork will allow for the sustained effect of the agent for many weeks to many months, and can be a replacement for the topical administration (e.g., eyedrops) of currently used glaucoma drugs. The methods described herein can be used to develop drug depots and, importantly, allow for the easy delivery of these agents in a doctor's office and can be done repeatedly.

One aspect of the present disclosure provides a method of delivering an ophthalmic agent to the aqueous outflow system of the eye a subject comprising placing the elastomeric material as described herein around the equator of the eye thereby occluding venous blood flow within the episcleral vein, administering via the episcleral vein a therapeutically effective amount of the ophthalmic agent, and removing the elastomeric material from the eye.

Another aspect of the present disclosure provides a method of delivering an ophthalmic agent to the anterior chamber of the eye comprising placing the elastomeric material as described herein around the equator of the eye thereby occluding venous blood flow within the episcleral vein, administering via the episcleral vein a therapeutically effective amount of the ophthalmic agent such that the ophthalmic agent is delivered to the anterior chamber of the eye and removing the elastomeric material from the eye.

Yet another aspect of the present disclosure provides methods for increasing the aqueous humor outflow in the eye of a subject suffering from glaucoma comprising placing the elastomeric material as described herein around the equator of the eye thereby occluding venous blood flow within the episcleral vein, administering via the episcleral vein a therapeutically effective amount of an ophthalmic agent and removing the elastomeric material from the eye.

The term "ophthalmic agent" as it is used herein is intended to encompass all agents which provide a local or systemic physiological or pharmacological effect when administered to mammals, including without limitation any specific drugs noted in the following description and analogs, derivatives, pharmaceutically acceptable salts, esters, prodrugs, codrugs, and protected forms thereof. In certain embodiments, the drug is a small molecule having a molecular weight of less than 1000 amu. For example, the drug may be a small molecule having a molecular weight of less than or equal to about 750 amu, 500 amu, 450 amu, 400 amu, 350 amu, or less than or equal to about 300 amu.

Many different ophthalmic agents may be incorporated into the device described herein. For example, suitable agents include outflow increasing agents, steroids, alpha receptor agonists, beta receptor antagonists, carbonic anhydrase inhibitors, adrenergic agents, physiologically active peptides and/or proteins, antineoplastic agents, antibiotics, analgesics, anti-inflammatory agents, muscle relaxants, antiepileptics, anti-ulcerative agents, anti-allergic agents, cardiotonics, anti-arrhythmic agents, vasodilators, antihypertensive agents, anti-diabetic agents, anti-hyperlipidemics, anticoagulants, hemolytic agents, antituberculous agents, hormones, narcotic antagonists, osteoclastic suppressants, osteogenic promoters, angiogenesis suppressors, antibacterials, non-steroidal anti-inflammatory drugs (NSAIDs), glucocorticoids or other anti-inflammatory corticosteroids, alkaloid analgesics, such as opioid analgesics, antivirals, such as nucleoside antivirals or a non-nucleoside antivirals, anti-benign prostatic hypertrophy (BPH) agents, anti-fungal compounds, antiproliferative compounds, anti-glaucoma compounds, immunomodulatory compounds, cell transport/mobility impeding agents, cytokines pegylated agents, alpha-blockers, anti-androgens, anti-cholinergic agents, purinergic agents, dopaminergic agents, local anesthetics, vanilloids, nitrous oxide inhibitors, anti-apoptotic agents, macrophage activation inhibitors, antimetabolites, neuroprotectants, calcium channel blockers, gamma-aminobutyric acid (GABA) antagonists, alpha agonists, anti-psychotic agents, tyrosine kinase inhibitors, nucleoside compounds, and nucleotide compounds, and analogs, derivatives, pharmaceutically acceptable salts, esters, prodrugs, codrugs, and protected forms thereof, and gene delivery agents, such as but not limited to, lentiviruses and the like.

Suitable NSAIDs include diclofenac, etoldolac, fenoprofen, floctafenine, flurbiprofen, ibuprofen, indoprofen, ketoprofen, ketorolac, lornoxicam, morazone, naproxen, perisoxal, pirprofen, pranoprofen, suprofen, suxibuzone, tropesin, ximoprofen, zaltoprofen, zileuton, and zomepirac, and analogs, derivatives, pharmaceutically acceptable salts, esters, prodrugs, codrugs, and protected forms thereof.

Suitable carbonic anhydrase inhibitors include brinzolamide, acetazolamide, methazolamide, dichlorphenamide, ethoxzolamide, and dorzolamide, and analogs, derivatives, pharmaceutically acceptable salts, esters, prodrugs, codrugs, and protected forms thereof.

Suitable adrenergic agents include brimonidine, apraclonidine, bunazosin, levobetaxolol, levobunalol, carteolol, isoprenaline, fenoterol, metipranolol, and clenbuterol, and analogs, derivatives, pharmaceutically acceptable salts, esters, prodrugs, codrugs, and protected forms thereof.

Suitable alpha receptor agonists include brimonidine and analogs, derivatives, pharmaceutically acceptable salts, esters, prodrugs, codrugs, and protected forms thereof.

Suitable beta receptor antagonists include betaxolol and timolol, and analogs, derivatives, pharmaceutically acceptable salts, esters, prodrugs, codrugs, and protected forms thereof.

Suitable antiviral agents include neviripine and analogs, derivatives, pharmaceutically acceptable salts, esters, prodrugs, codrugs, and protected forms thereof.

Suitable alkaloid analgesics include desmorphine, dezocine, dihydromorphine, eptazocine, ethylmorphine, glafenine, hydromorphone, isoladol, ketobenidone, p-lactophetide, levorphanol, moptazinol, metazocin, metopon, morphine, nalbuphine, nalmefene, nalorphine, naloxone, norlevorphanol, normorphine, oxmorphone, pentazocine, phenperidine, phenylramidol, tramadol, and viminol, and analogs, derivatives, pharmaceutically acceptable salts, esters, prodrugs, codrugs, and protected forms thereof.

Suitable glucocorticoids include 21-acetoxypregnenolone, alclometasone, algestone, anacortave acetate, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, diflorasone, diflucortolone, difuprednate, enoxolone, fluazacort, flucloronide, flumethasone, flunisolide, fluocinolone acetonide, fluocinonide, flucloronide, flumethasone, flunisolide, fluocortin butyl, fluocortolone, fluorometholone, fluperolone acetate, fluprednisolone, flurandrenolide, fluticasone propionate, hydrocortamate, hydrocortisone, meprednisone, methylprednisolone, paramethasone, prednisolone, prednisolone 21-diethylaminoacetate, fluprednidene acetate, formocortal, loteprednol etabonate, medrysone, mometasone furoate, prednicarbate, prednisolone, prednisolone 25-diethylaminoacetate, prednisolone sodium phosphate, prednisone, prednival, prednylidene, triamcinolone, triamcinolone acetonide, triamcinolone benetonide, and triamcinolone hexacetonide, and analogs, derivatives, pharmaceutically acceptable salts, esters, prodrugs, codrugs, and protected forms thereof.

Other suitable steroids include halcinonide, halbetasol propionate, halometasone, halopredone acetate, isofluprednone, loteprednol etabonate, mazipredone, rimexolone, and tixocortol, and analogs, derivatives, pharmaceutically acceptable salts, esters, prodrugs, codrugs, and protected forms thereof.

Suitable BPH drugs include finasteride and osaterone, and analogs, derivatives, pharmaceutically acceptable salts, esters, prodrugs, codrugs, and protected forms thereof.

Suitable antibacterial compounds include capreomycins, including capreomycin IA, capreomycin IB, capreomycin IIA and capreomycin IIB; carbomycins, including carbomycin A; carumonam; cefaclor, cefadroxil, cefamandole, cefatrizine, cefazedone, cefazolin, cefbuperazone, cefcapene pivoxil, cefclidin, cefdinir, cefditoren, cefime, ceftamet, cefmenoxime, cefmetzole, cefminox, cefodizime, cefonicid, cefoperazone, ceforanide, cefotaxime, cefotetan, cefotiam, cefoxitin, cefpimizole, cefpiramide, cefpirome, cefprozil, cefroxadine, cefsulodin, ceftazidime, cefteram, ceftezole, ceftibuten, ceftiofur, ceftizoxime, ceftriaxone, cefuroxime, cefuzonam, cephalexin, cephalogycin, cephaloridine, cephalosporin C, cephalothin, cephapirin, cephamycins, such as cephamycin C, cephradine, chlortetracycline; chlarithromycin, clindamycin, clometocillin, clomocycline, cloxacillin, cyclacillin, danofloxacin, demeclocyclin, destomycin A, dicloxacillin, dicloxacillin, dirithromycin, doxycyclin, epicillin, erythromycin A, ethanbutol, fenbenicillin, flomoxef, florfenicol, floxacillin, flumequine, fortimicin A, fortimicin B, forfomycin, foraltadone, fusidic acid, gentamycin, glyconiazide, guamecycline, hetacillin, idarubicin, imipenem, isepamicin, josamycin, kanamycin, leumycins such as leumycin A.sub.1, lincomycin, lomefloxacin, loracarbef, lymecycline, meropenam, metampicillin, methacycline, methicillin, mezlocillin, micronaomicin, midecamycins such as midecamycin A.sub.1, mikamycin, minocycline, mitomycins such as mitomycin C, moxalactam, mupirocin, nafcillin, netilicin, norcardians such as norcardian A, oleandomycin, oxytetracycline, panipenam, pazufloxacin, penamecillin, penicillins such as penicillin G, penicillin N and penicillin O, penillic acid, pentylpenicillin, peplomycin, phenethicillin, pipacyclin, piperacilin, pirlimycin, pivampicillin, pivcefalexin, porflromycin, propiallin, quinacillin, ribostamycin, rifabutin, rifamide, rifampin, rifamycin SV, rifapentine, rifaximin, ritipenem, rekitamycin, rolitetracycline, rosaramicin, roxithromycin, sancycline, sisomicin, sparfloxacin, spectinomycin, streptozocin, sulbenicillin, sultamicillin, talampicillin, teicoplanin, temocillin, tetracyclin, thostrepton, tiamulin, ticarcillin, tigemonam, tilmicosin, tobramycin, tropospectromycin, trovafloxacin, tylosin, and vancomycin, and analogs, derivatives, pharmaceutically acceptable salts, esters, prodrugs, codrugs, and protected forms thereof.

Antiproliferative/antimitotic drugs and prodrugs include natural products such as vinca alkaloids (e.g., vinblastine, vincristine, and vinorelbine), paclitaxel, epidipodophyllotoxins (e.g., etoposide, teniposide), antibiotics (e.g., actinomycins, daunorubicin, doxorubicin and idarubicin), anthracyclines, mitoxantrone, bleomycins, plicamycin (mithramycin) and mitomycin, enzymes (e.g., L-asparaginase); antiplatelet prodrugs; antiproliferative/antimitotic alkylating prodrugs such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), triazenes, dacarbazine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine (cladribine); platinum coordination complexes (cisplatin, carboplatin), procarbazine, hydroxyurea, mitotane, aminoglutethimide; hormones (e.g., estrogen, progestin); anticoagulants (e.g., heparin, synthetic heparin salts and other inhibitors of thrombin); fibrinolytic prodrugs such as tissue plasminogen activator, streptokinase and urokinase, aspirin, dipyridamole, ticlopidine, clopidogrel, abciximab; antimigratory; antisecretory (breveldin); anti-inflammatory agents such as corticosteroids (cortisol, cortisone, fludrocortisone, flucinolone, prednisone, prednisolone, methylprednisolone, triamcinolone, betamethasone, and dexamethasone), NSAIDS (salicylic acid and derivatives, aspirin, acetaminophen, indole and indene acetic acids (indomethacin, sulindac and etodalac), heteroaryl acetic acids (tolmetin, diclofenac, and ketorolac), arylpropionic acids (e.g., ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives (e.g., cyclosporine, tacrolimus (FK-506), sirolimus (rapamycin), azathioprine, and mycophenolate mofetil); angiogenic agents such as vascular endothelial growth factor (VEGF), fibroblast growth factor (FGF); angiotensin receptor blocker; nitric oxide donors; anti-sense oligonucleotides and combinations thereof; cell cycle inhibitors, mTOR inhibitors, growth factor signal transduction kinase inhibitors, neovascularization inhibitors, angiogenesis inhibitors, and apoptosis inhibitors, and analogs, derivatives, pharmaceutically acceptable salts, esters, prodrugs, codrugs, and protected forms thereof.

In certain embodiments, the ophthalmic agent comprises an outflow agent. As used herein, the term "outflow increasing agent" refers to those agents which are capable of increasing aqueous humor outflow in the eye, thereby relieving intraocular pressure in the eye.

In certain embodiments, the outflow increasing agent comprises ethacrynic acid (which is [2,3-dichloro-4-(2-methylene-1-oxobutyl)phenoxy]acetic acid) or any analog, salt, or derivative thereof. Ethacrynic acid and its salts, derivatives, and analogs, along with preferred methods of administering these compounds are described in detail in U.S. Pat. Nos. 3,255,241, 4,757,089, 5,306,731, 5, 458,883, 5,863,948, 6,126,957, and 6,534,082, the contents of which are hereby incorporated by reference in their entirety.

In certain embodiments, the increasing agent comprises ethacrynic acid derivatives and analogs, which may or may not comprise a sulfhydryl reactive moiety. Exemplary agents include, but are not limited to: 2-[2,3-dichloro-4-[(Z)-2-methylbut-2-enoyl]phenoxy]acetic acid, 2-[2,3-dichloro-4-(3-methylbut-2-enoyl)phenoxy]acetic acid, 2-[2,3-dichloro-4-(2-methylidenebutanoyl)phenoxy]-2-(2,3-dihydroxypropoxy)acetic acid, [(2S,3R,4R)-1,3,4,5-tetrahydroxypentan-2-yl]-2-[2,3-dichloro-4-(2-methylidenebutanoyl)phenoxy]acetate, 2-[2,3-dichloro-4-(2,3-dimethylbutanoyl)phenoxy]acetic acid, etc.

In certain embodiments, the increasing agent comprises ethacrynic acid derivatives and analogs, which comprise a sulfhydryl reactive moiety. In certain embodiments, the increasing agent comprises ethacrynic acid thiol addicts. Examples include, but are not limited to, ethacrynic acid-L-cysteine (i.e., S-[2-[4-(Carboxymethoxy)-2,3-dichlorobenzoyl]butyl]-L-cysteine), ethacrynic acid-cysteamine (i.e., 2-(4-(2-((2-aminoethylthio)methyl)butanoyl)-2,3-dichlorophenoxy)acetic acid), ethacrynic acid-glutathione (i.e., 2-amino-5-(3-(2-(4-(carboxymethoxy)-2,3-dichlorobenzoyl)butylthio)-1-(carboxymethylamino)-1-oxopropan-2-ylamino)-5-oxopentanoic acid), ethacrynic acid-thiosalicylic acid (2-(2-(4-(carboxymethoxy)-2,3-dichlorobenzoyl)butylthio)benzoic acid), ethacrynic acid-N-acetylcysteine (2-acetamido-3-(2-(4-(carboxymethoxy)-2,3-dichlorobenzoyl)butylthio)propanoic acid), ethacrynic acid-N-acetylcysteamine (i.e., 2-(4-(2-((2-acetamidoethylthio)methyl)butanoyl)-2,3-dichlorophenoxy)acetic acid), or any salt thereof.

In other embodiments, the increasing agent is ethacrynic acid-L-cysteine (i.e., S-[2-[4-(Carboxymethoxy)-2,3-dichlorobenzoyl]butyl]-L-cysteine), or any salt thereof.

In another embodiments, the increasing agent is 2-[2,3-dichloro-4-[2-(methyl-sulfanylmethyl)butanoyl]phenoxy]acetic acid.

In another embodiment, the increasing agent comprises phenoxyacetic acid, 2,3-dichlorophenoxyacetic acid, 2,4-dichlorophenoxyacetic acid, or any analog or derivative thereof. In one embodiment, the increasing agent comprises phenoxyacetic acid, 2,3-dichlorophenoxyacetic acid, or 2,4-dichlorophenoxyacetic acid derivative which is non-SH reactive. In certain embodiments, the non-SH reactive phenoxyacetic acid derivative comprises indacrinone (i.e., 6,7-dichloro-2-methyl-1-oxo-2-phenyl-5-indanyloxyacetic acid), ticrynafen (i.e., 2-(2,3-dichloro-4-(thiophene-2-carbonyl)phenoxy)acetic acid), or any salt thereof.

Yet another aspect of the present disclosure provides a method of inducing a glaucoma-like condition in a subject comprising placing the elastomeric material as described herein around the equator of the eye thereby occluding venous blood flow within the episcleral vein, administering via the episcleral vein an effective amount of an ophthalmic agent and a viscoelastic agent and removing the elastomeric material from the eye.

As used herein, the term "glaucoma-like condition" refers to any condition which presents symptoms and/or conditions that are associated with glaucoma, such as increased intraocular pressure and/or optic nerve damage. Also included in this definition are conditions such as elevated intraocular pressures in the setting of hypotony, such as after glaucoma surgery or situations related to uveitis.

In other embodiments, the ophthalmic agent is administered with a viscoelastic agent. As used herein, the term "viscoelastic agent" refers to any agent capable of expanding the anterior chamber of the eye to allow for delivery of additional compounds and/or surgical instruments. Suitable viscoelastic agents include, but are not limited to, Healon®OVD, Healon5®OVD, HealonGV®, Provic® and the like. In certain embodiments, the ratio of ophthalmic agent to viscoelastic agent is 3:1.

In some embodiments, the viscoelastic agent is administered before the ophthalmic agent. In other embodiments, the viscoelastic agent is administered concurrently with the ophthalmic agent. In yet other embodiments, the viscoelastic agent is administered after the ophthalmic agent.

The present disclosure further provides pharmaceutical compositions comprising an ophthalmic agent described herein, optionally a viscoelastic agent, and a pharmaceutically acceptable carrier. As used herein, the term "pharmaceutical composition" refers to the combination of at least one ophthalmic agent as described herein with a carrier, inert or active, making the composition especially suitable for diagnostic or therapeutic use in vivo, in vitro, or ex vivo. In certain embodiments, the pharmaceutical composition comprises an ophthalmic agent and a viscoelastic agent. A "pharmaceutically acceptable carrier" refers to any of the standard pharmaceutical carriers, such as a phosphate buffered saline solution, water, emulsions (e.g., such as an oil/water or water/oil emulsions), various types of wetting agents, diluents, and excipients. The compositions also can include stabilizers and preservatives. For examples of carriers, stabilizers and adjuvants. (See e.g., Martin, Remington's Pharmaceutical Sciences, 15th Ed., Mack Publ. Co., Easton, Pa. (1975)).

The pharmaceutical composition is typically prepared as a solution in tolerable (acceptable) diluent such as saline, phosphate-buffered saline or other physiologically tolerable diluent and the like to form an aqueous pharmaceutical composition.

The route of administration may be intravenous (I.V.), intramuscular (I.M.), subcutaneous (S.C.), intradermal (I.D.), intraperitoneal (I.P.), intratumor and the like, which results in eliciting a desired response. Additional methods of administration can include topical administration (eye drops), subconjunctival, intracameral, periocular or intravitreal injection or introduction by balloon catheter or ophthalmic inserts surgically placed in the conjunctival sac. In preferred embodiments, the route of administration is via injection into the episcleral vein.

The therapeutic dosage of the compositions can vary according to, for example, the manner of administration of the compound, the health and condition of the patient, and the judgment of the prescribing physician. The proportion or concentration of an ophthalmic agent described herein in a pharmaceutical composition can vary depending upon a number of factors including dosage, chemical characteristics (e.g., hydrophobicity), and the route of administration. For example, the ophthalmic agents described herein can be provided in an aqueous physiological buffer solution containing about 0.1 to about 10% w/v of the agent. Some typical dose ranges are from about 1 µg/kg to about 1 g/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems. In one embodiment, the dose is administered at least once. Subsequent doses may be administered as indicated.

EXAMPLES

The methods and materials of the disclosure are further illustrated by the following examples, which are not to be construed as limiting the disclosure in scope and are offered by way of illustration.

Example 1

Figure 4:
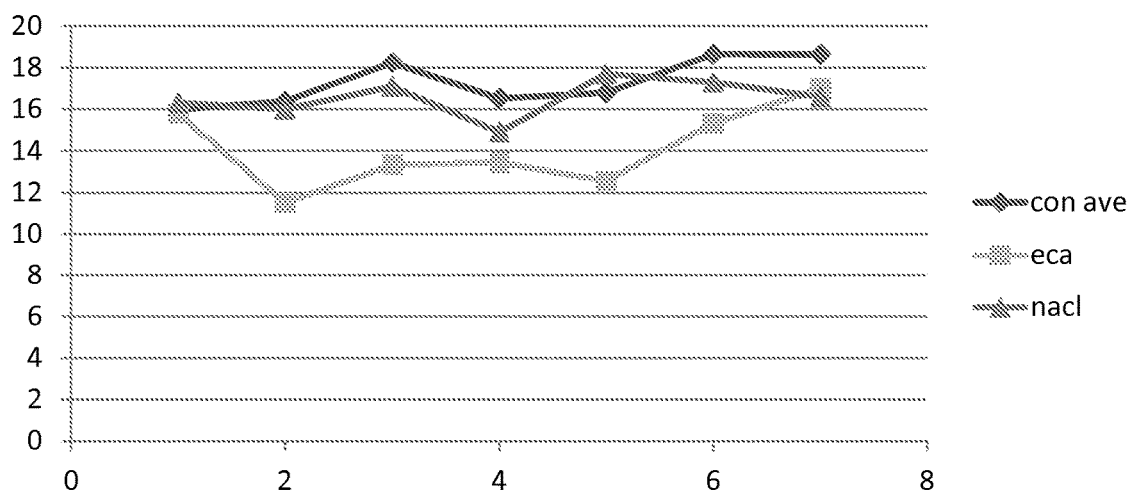
FIG. 4 is a graph and associated data showing the effects of ECA injection into the episcleral vein using an embodiment of the present disclosure.
Figure 5:
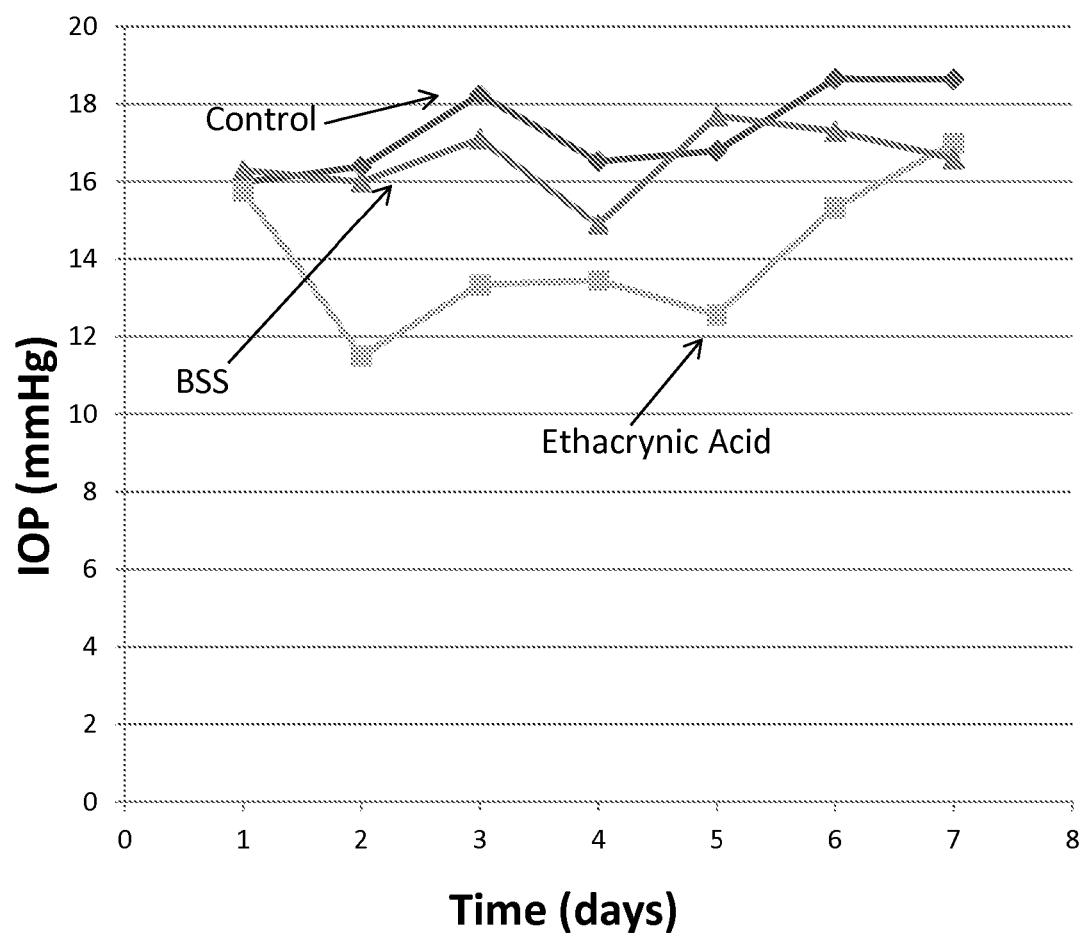
FIG. 5 is a graph showing the addition of ethacrynic acid reduces intraocular pressure (IOP) greater than control.
Figure 6:
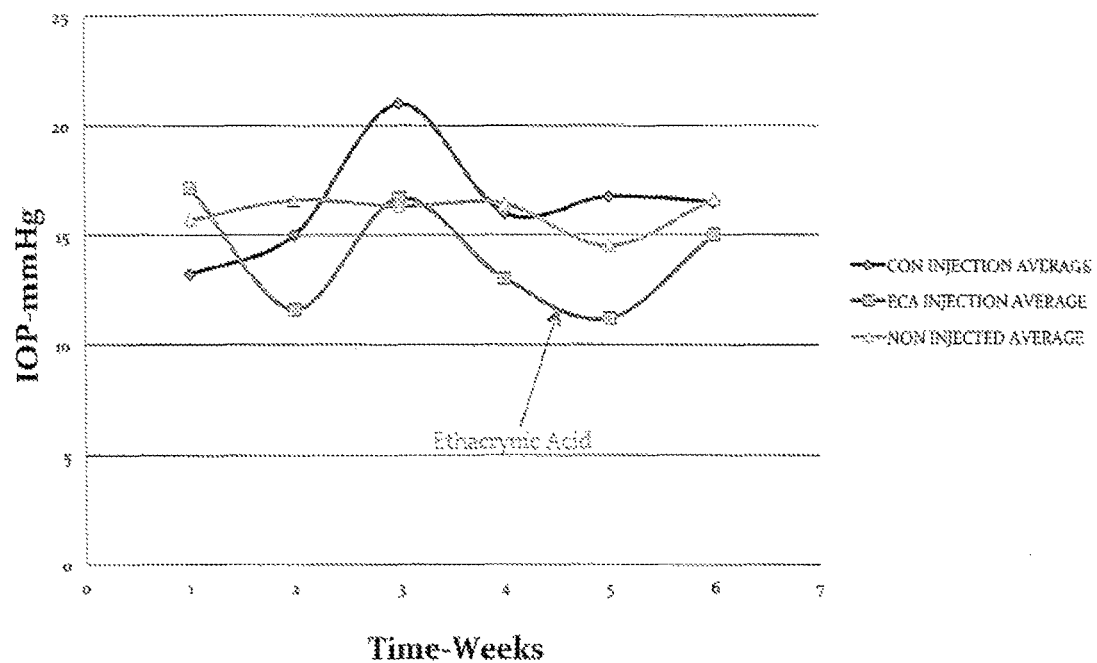
FIG. 6 is a graph showing that mice injected with the ECA+Healon mixture had lower average IOP levels than mice injected with BSS (control [con]) or no injection.

Effect of Direct Injection of Ethacrinic Acid (ECA) with and without Healon Via the Episcleral Vein Basline intraocular pressures were measured in both eyes of the mouse using a TonoLab device. A piece of a latex glove was placed over the equator of the mouse eye. Initially, a glass microcannula was used to inject either (a) a solution of ethacrynic acid alone or (b) saline into the episcleral vein at the limbus of the right eye of each mouse. The solution or saline was injected until blanching was observed 360 degrees around the limbus. The piece of latex was then removed from the eye. Intraocular pressures were then measured daily and then weekly in both eyes of all mice. The ethacrynic acid injection alone produced its most profound effect at day 2; however, some effect was maintained until day 7. The results of the above protocol are provided in Table 1, and also shown in FIG. 4, where ethacrynic acid is noted as ECA (squares), saline control is BSS (triangles), and non-treated control is control (diamonds).

TABLE 1

| Label | 0 hr OD base | 0 hr OS CON | 1 day OD BSS | 1 day OS CON | 2 day OD BSS | 2 day OS CON | 5 day OD BSS | 5 day OS CON | 6 day OD BSS | 6 day OS CON | 1 wk OD BSS | 1 wk OS CON |
|---|---|---|---|---|---|---|---|---|---|---|---|---|
| CON1 | 15 | 18 | 18 | 17 | 30 | 15 | 25 | 17 | 25 | 22 | 21 | 18 |
| CON2 | 15 | 16 | | | | | | | | | | |
| CON3 | 13 | 12 | 14 | 17 | 18 | 14 | 14 | 16 | 15 | 14 | 16 | 12 |
| CON4 | 12 | 13 | 14 | 21 | 18 | 20 | 12 | 19 | 12 | 16 | 14 | 17 |
| CON5 | 11 | 14 | 14 | 16 | 18 | 11 | 13 | 17 | 15 | 18 | 15 | 17 |
| Avg. | 13.2 | 14.6 | 15 | 17.75 | 21 | 15 | 16 | 17.25 | 16.75 | 17.5 | 16.5 | 16 |
| ECA1 | 13 | 12 | 14 | 18 | 12 | 15 | 13 | 16 | 10 | 9 | 16 | 16 |
| ECA2 | 16 | 18 | 13 | 15 | 19 | 16 | 8 | 7 | 9 | 12 | 12 | 15 |
| ECA4 | 18 | 14 | 9 | 16 | 12 | 20 | 17 | 20 | 7 | 12 | 14 | 17 |
| ECA5 | 20 | 18 | 13 | 17 | 19 | 17 | 14 | 18 | 10 | 13 | 18 | 21 |
| ECA6 | 16 | | — | | 22 | | 16 | | 20 | | dead | |
| Avg. | 16.6 | 15.5 | 12.25 | 16.5 | 16.8 | 17 | 13.6 | 15.25 | 11.2 | 11.5 | 15 | 17.25 |

Figure 3:
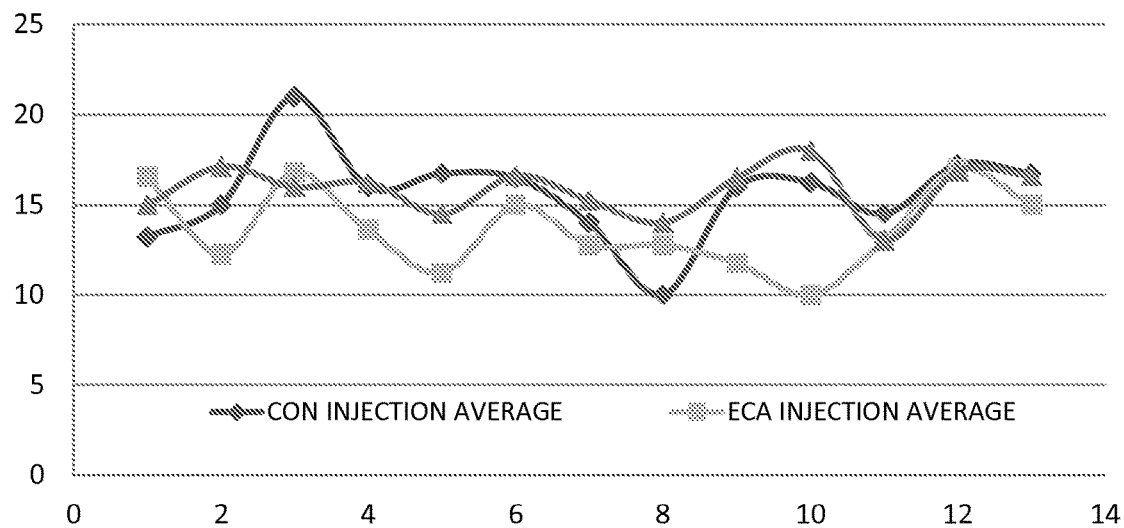
FIG. 3 is a graph and associated data showing the effects of ECA injection into the episcleral vein using an embodiment of the present disclosure.

Next, ethacrynic acid was combined with healon in a 3:1 ratio. Again, a glass microcannula was used to inject either the ethacrynic acid/healon solution or BSS solution as the control. The ethacrynic acid/healon solution produced its most profound effect at 2 weeks but lasted 3 weeks. The results are provided in Table 2 and also shown in FIG. 3, where ethacrynic acid/healon is designated with squares, BSS as diamonds, and non injected controls as triangles.

TABLE 2

| Label | 0 hr OD base | 0 hr OS CON | 1 day OD BSS | 1 day OS CON | 2 day OD BSS | 2 day OS CON | 5 day OD BSS | 5 day OS CON | 7 day OD BSS | 7 day OS CON | 14 day OD BSS | 14 day OS CON |
|---|---|---|---|---|---|---|---|---|---|---|---|---|
| CON1 | 15 | 18 | 18 | 17 | 30 | 15 | 25 | 17 | 25 | 22 | 21 | 18 |
| CON2 | 15 | 16 | | | | | | | | | | |
| CON3 | 13 | 12 | 14 | 17 | 18 | 14 | 14 | 16 | 15 | 14 | 16 | 12 |
| CON4 | 12 | 13 | 14 | 21 | 18 | 20 | 12 | 19 | 12 | 16 | 14 | 17 |
| CON5 | 11 | 14 | 14 | 16 | 18 | 11 | 13 | 17 | 15 | 18 | 15 | 17 |
| Avg. | 13.2 | 14.6 | 15 | 17.75 | 21 | 15 | 16 | 17.25 | 16.75 | 17.5 | 16.5 | 16 |
| ECA1 | 13 | 12 | 14 | 18 | 12 | 15 | 13 | 16 | 10 | 9 | 16 | 16 |
| ECA2 | 16 | 18 | 13 | 15 | 19 | 16 | 8 | 7 | 9 | 12 | 12 | 15 |
| ECA4 | 18 | 14 | 9 | 16 | 12 | 20 | 17 | 20 | 7 | 12 | 14 | 17 |
| ECA5 | 20 | 18 | 13 | 17 | 19 | 17 | 14 | 18 | 10 | 13 | 18 | 21 |
| ECA6 | 16 | | — | | 22 | | 16 | | 20 | | dead | |
| Avg. | 16.6 | 15.5 | 12.25 | 16.5 | 16.8 | 17 | 13.6 | 15.25 | 11.2 | 11.5 | 15 | 17.25 |
| ECA3 | 20 | 22 | 9 | 11 | 16 | 20 | 10 | 17 | 10 | 16 | 18 | 16 |

TABLE 2-continued

| Label | 21 day OD base | 21 day OS CON | 35 day OD BSS | 35 day OS CON | 42 day OD BSS | 42 day OS CON | 56 day OD BSS | 56 day OS CON | 64 day OD BSS | 64 day OS CON | 74 day OD BSS | 74 day OS CON | 74 day OD BSS | 74 day OS CON |
|---|---|---|---|---|---|---|---|---|---|---|---|---|---|---|
| CON1 | 12 | 19 | 8 | 12 | 12 | 16 | 18 | 19 | 14 | 13 | 17 | 16 | 15 | 17 |
| CON2 |  |  |  |  |  |  |  |  | 16 | 12 | 18 | 17 | 17 | 18 |
| CON3 | 19 | 19 | 9 | 13 | 19 | 16 | 13 | 13 |  |  |  |  |  |  |
| CON4 | 15 | 17 | 7 | 8 | 15 | 19 | 13 | 17 | 17 | 18 | 18 | 19 | 16 | 18 |
| CON5 | 10 | 11 | 16 | 20 | 18 | 19 | 21 | 20 | 11 | 13 | 16 | 17 | 19 | 18 |
| Avg. | 14 | 16.5 | 10 | 13.25 | 16 | 17.5 | 16.25 | 17.25 | 14.5 | 14 | 17.25 | 17.25 | 16.75 | 17.75 |
| ECA1 | 16 | 18 | 11 | 9 | 15 | 18 | 13 | 20 | 16 | 13 | 19 | 19 | 17 | 17 |
| ECA2 | 7 | 13 | 8 | 11 | 12 | 16 | 10 | 22 | 12 | 9 | 14 | 15 | 11 | 12 |
| ECA4 | 14 | 14 | 15 | 21 | 8 | 14 | 7 | 14 | 9 | 11 | 17 | 17 | 16 | 15 |
| ECA5 | 14 | 11 | 17 | 18 | 12 | 14 | 10 | 19 | 15 | 15 | 18 | 15 | 16 | 18 |
| ECA6 |  |  |  |  |  |  |  |  |  |  |  |  |  |  |
| Avg. | 12.75 | 14 | 12.75 | 13.92 | 14.11 | 16.61 | 13.47 | 17.92 | 13.83 | 13.11 | 17 | 17 | 19 | 21 |
| ECA3 | 8 | 10 | 14 | 17 | 11 | 12 | 17 | 19 | 14 | 14 |  |  |  |  |

Example 2

The Impact of Sustained Delivery of Ethacrist (Ethacrynic Acid+L-Cysteine) Sustained-Release Nanoparticles on Intraocular Pressure (IOP)

Example 2.1

To test whether sustained release of Ethacrynic Acid (ECA) nanoparticles (without healon) injected into the episcleral vein can lower intraocular pressures over extended periods of time for patients suffering from glaucoma, the right eye of 8 C57Bl6 mice were injected with either ethacrist nanoparticles (without healon) (4 mice) or balanced salt solution (BSS) (4 mice) into the episcleral vein at the limbus. Baseline IOPs were measured with the rodent Tono-Lab™ device prior to the injections, and then weekly. Slit lamp exams were performed to evaluate conjunctival redness, inflammation in the anterior chamber, and cloudiness of the cornea.

Figure 7A:
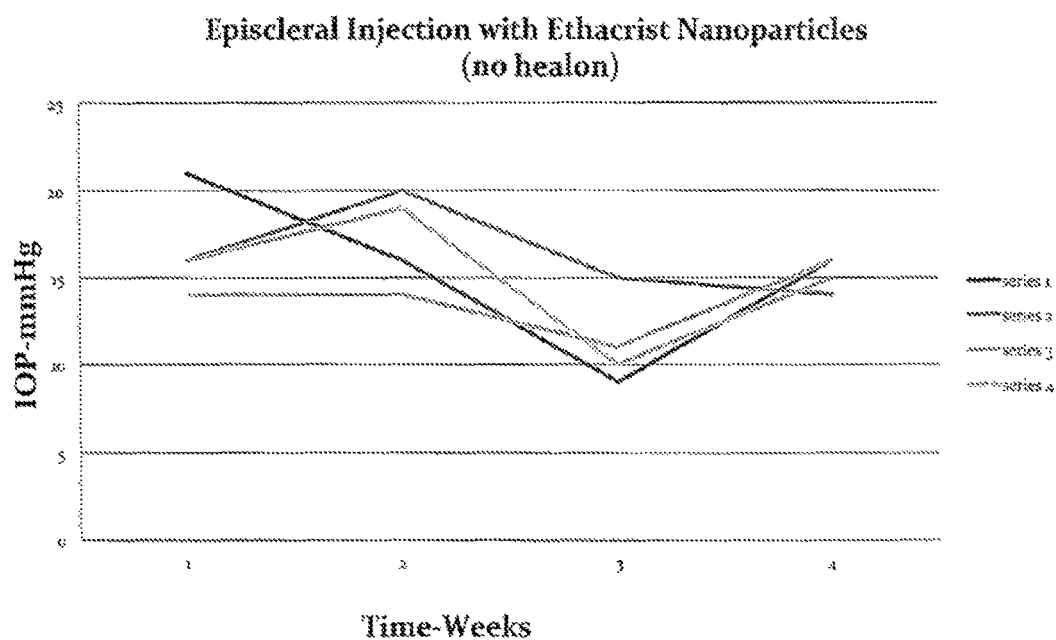
FIG. 7 are graphs showing the results of IOP in mice after episcleral injection of ethacrist nanoparticles. (a) episcleral injection of mice with ethacrist nanoparticles (no Healon); (b) ethacrist nanoparticles+Healon (3:1 ratio); and (c) BSS (control).

As shown in FIG. 7a, all 4 mice (labeled "series 1, 2, 3, and 4") showed a profound drop in IOP at 3 weeks, with an eventual return to baseline at 4 weeks.

Example 2.2

To test whether viscoelastic healon, or similar compound, prolongs the IOP-lowering effects of ethacrist nanoparticles, the right eye of 6 C57Bl6 mice were injected with either ethacrist nanoparticles plus healon in a 3:1 ratio (3 mice) or BSS (3 mice). Baseline IOPs were measured with the rodent TonoLab™ device prior to the injections and then weekly thereafter. Slit lamp exams were performed to evaluate conjunctival redness, inflammation in the anterior chamber, and cloudiness of the cornea.

Figure 10:
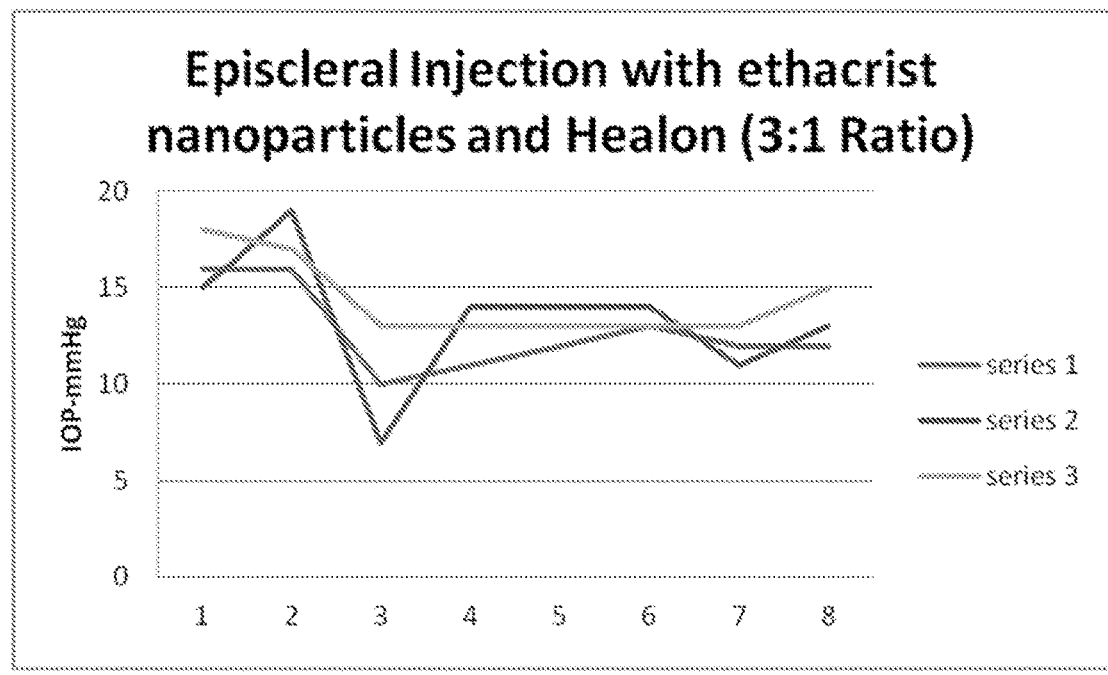
FIG. 10 is a graph showing the effect of the episcleral vein injection of ethacrist nanoparticles combined with healon in a 3:1 in mice.

The graph in FIG. 10 shows that mice with episcleral vein injection of ethacrist nanoparticles combined with healon in a 3:1 ratio had a profound drop in IOP at 3 weeks which extended to 8 weeks.

Example 2.3

Figure 8A:
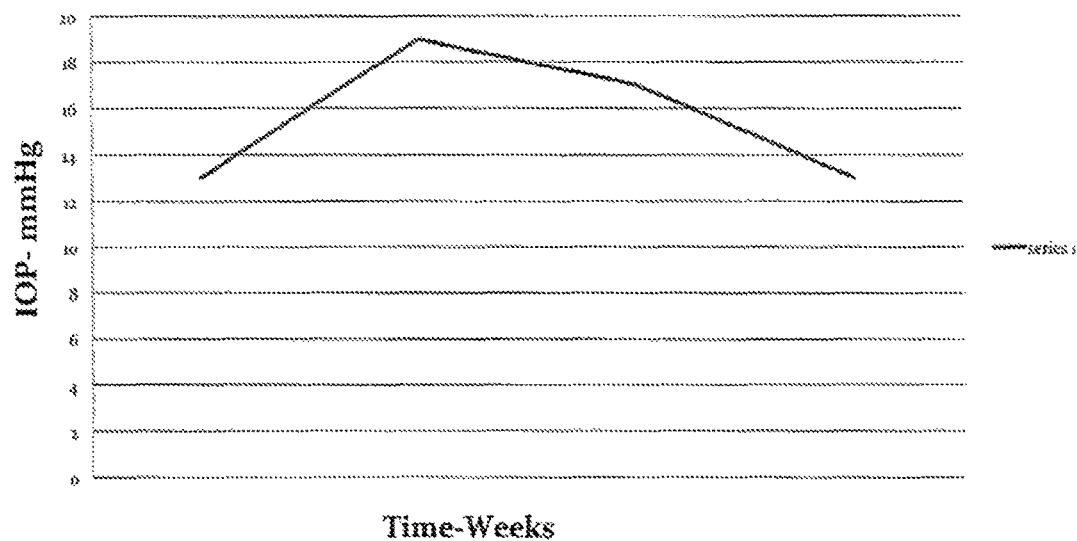
FIG. 8 are graphs showing the results of IOP in mice after intracameral injection of ethacrist nanoparticles comprising (a) high concentration of nanoparticles (10 µg/µl) or (b) low concentration (1 µg/µl) of nanoparticles.
Figure 8B:
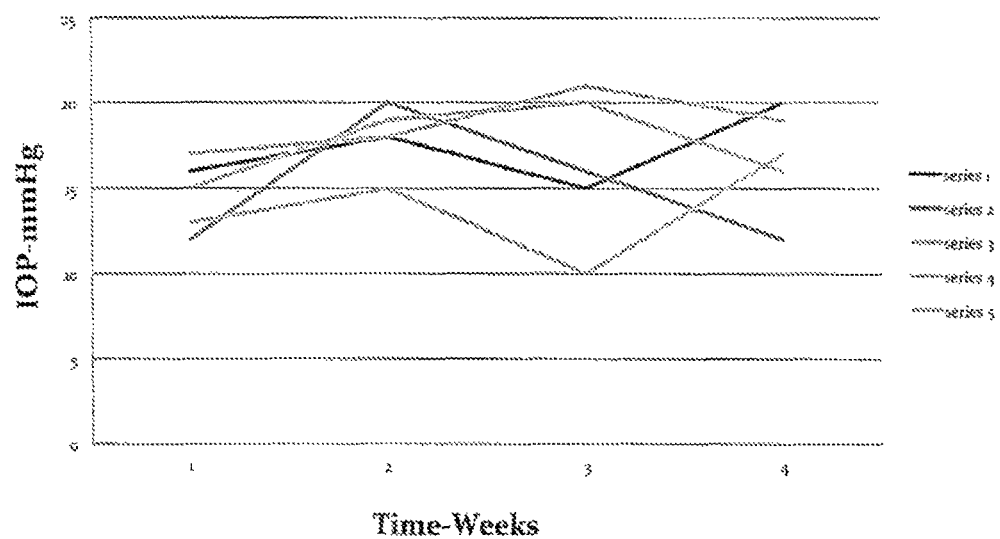
Figure 9A:
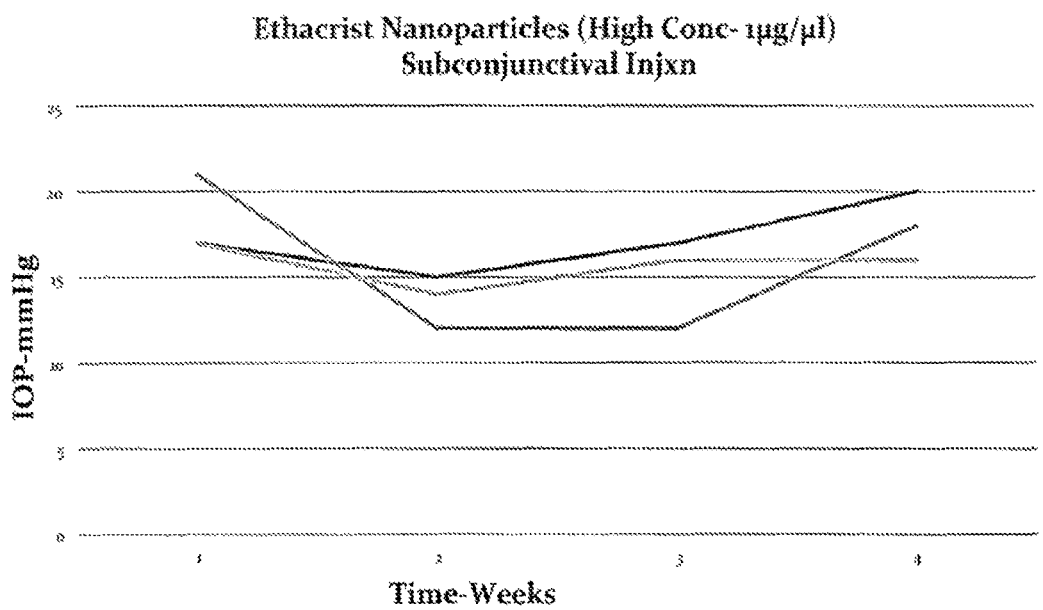
FIG. 9 are graphs showing the results of IOP in mice after subconjunctival injection of ethacrist nanoparticles comprising (a) a high concentration (1 µg/µl) or (b) low concentration (0:1 µg/µl) of nanoparticles.
Figure 9B:
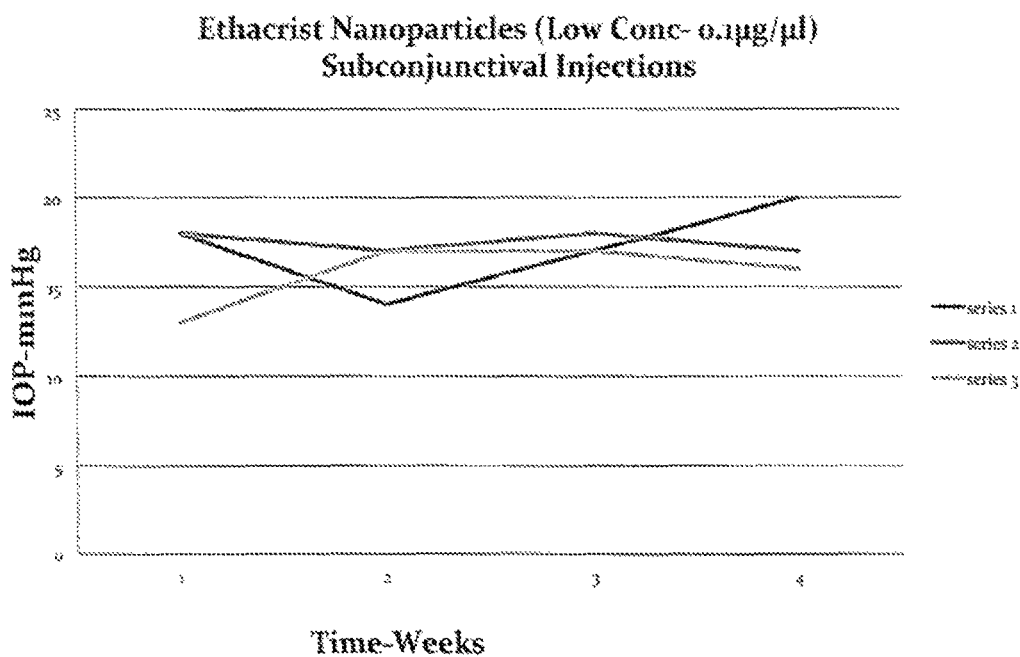

Other methods of ethacrist nanoparticles delivery were tested. Subconjunctival delivery is shown in FIGS. 9a and 9b (high and low concentrations of ethacrist nanoparticles), and intracameral delivery is shown in FIGS. 8a and 8b (high and low concentrations of ethacrist nanoparticles). Baseline IOPs were measured with the rodent TonoLab™ device prior to the injections and then weekly thereafter. Slit lamp exams were performed to evaluate conjunctival redness, inflammation in the anterior chamber, and cloudiness of the cornea.

Figure 7B:
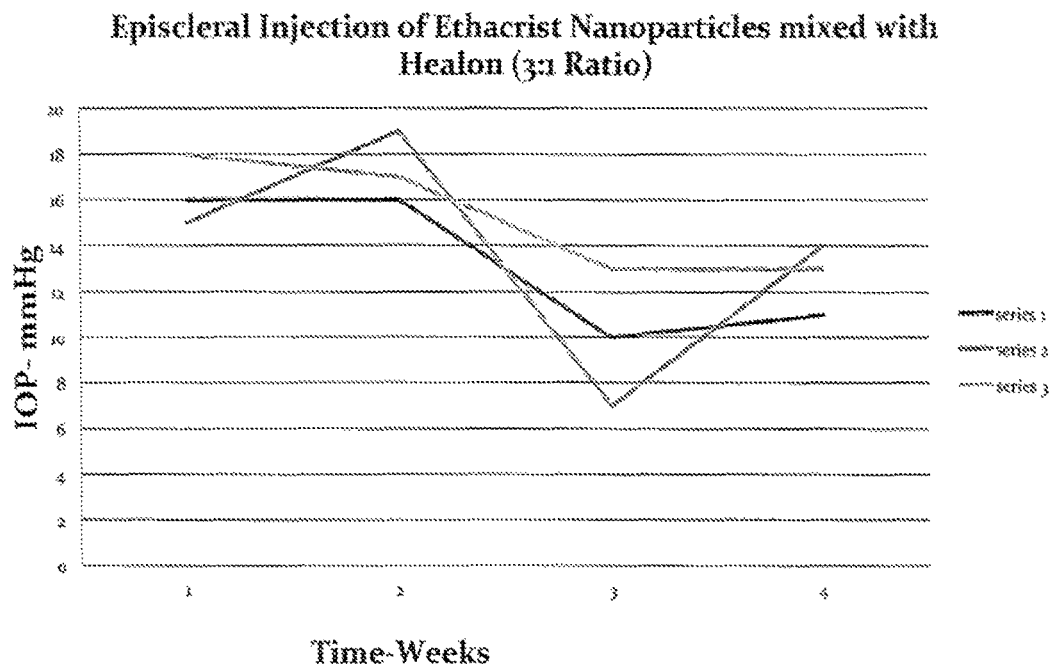
Figure 7C:
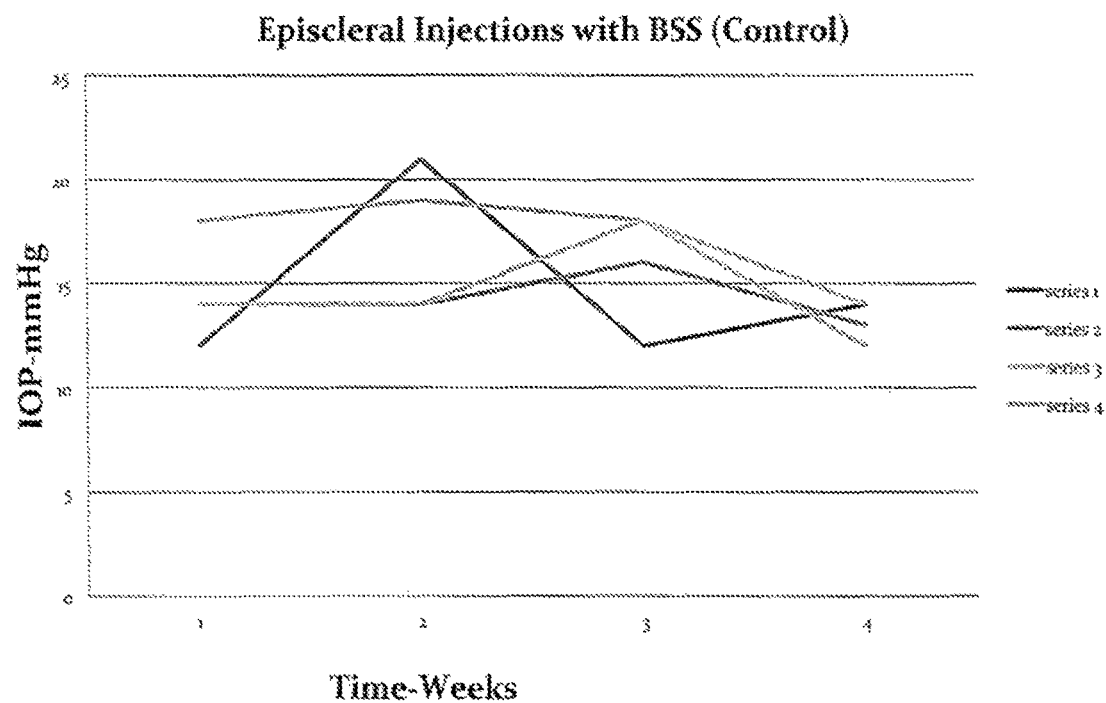

The graphs in FIGS. 7-9 shows the results of the following: FIG. 7a shows episcleral injection of mice with ethacrist nanoparticles (no Healon), FIG. 7b shows episcleral injection of ethacrist nanoparticles+Healon (3:1 ratio), and FIG. 7c shows episcleral injection of BSS (control); FIG. 8a shows intracameral injection of ethacrist nanoparticles comprising either a high concentration of nanoparticles (10 µg/µl) and FIG. 8b shows intracameral injection of low concentration (1 µg/µl) of nanoparticles; and FIGS. 9a-b show subconjunctival injection of ethracrist nanoparticles comprising either a 9a high concentration (1 µg/µl) (FIG. 9a) or low concentration (0.1 µg/µl) of nanoparticles (FIG. 9b). In all of these figures, each individual "series" represents an individual mouse.

The above results suggest that episcleral injections with Ethacrist nanoparticles appear superior to intracameral injections and subconjunctivial injections for lowering IOP. In addition, episcleral injections of Ethacrist nanoparticles mixed with healon (in a 3:1 ratio) appear to be better than nanoparticles alone at lowering the IOP.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods described herein are presently representative of preferred embodiments, are exemplary, and are not intended as limitations on the scope of the invention. Changes therein and other uses will occur to those skilled in the art which are encompassed within the spirit of the invention as defined by the scope of the claims.

We claim:
1. A method of increasing aqueous humor outflow in an eye of a subject suffering from glaucoma comprising: (a) placing an elastomeric material around the equator of the eye thereby occluding venous blood flow within the episcleral vein, wherein the elastomeric material comprises a planar body, and the body comprising: a central opening having an inner diameter and an outer diameter of at least 1 mm, wherein when the elastomeric material is configured to be placed upon the eye, the inner diameter portion is stretched to fit around the equator of the eye and, upon contraction, the venous blood flow within the episcleral vein of the eye is occluded; (b) administering to the episcleral vein an ophthalmic agent; and (c) removing the elastomeric material from the eye.

2. The method according to claim 1, wherein the ophthalmic agent is selected from the group consisting of steroids, alpha receptor agonists, beta receptor antagonists, carbonic anhydrase inhibitors, adrenergic agents, physiologically active peptides and/or proteins, antineoplastic agents, antibiotics, analgesics, anti-inflammatory agents, muscle relaxants, anti-epileptics, anti-ulcerative agents, anti-allergic agents, cardiotonics, anti-arrhythmic agents, vasodilators, antihypertensive agents, anti-diabetic agents, anti-hyperlipidemics, anticoagulants, hemolytic agents, antituberculous agents, hormones, narcotic antagonists, osteoclastic suppressants, osteogenic promoters, angiogenesis suppressors, antibacterials, non-steroidal anti-inflammatory drugs (NSAIDs), glucocorticoids or other anti-inflammatory corticosteroids, alkaloid analgesics, such as opioid analgesics, antivirals, such as nucleoside antivirals or a non-nucleoside antivirals, anti-benign prostatic hypertrophy (BPH) agents, anti-fungal compounds, antiproliferative compounds, anti-glaucoma compounds, immunomodulatory compounds, cell transport/mobility impeding agents, cytokines pegylated agents, alpha-blockers, anti-androgens, anti-cholinergic agents, purinergic agents, dopaminergic agents, local anesthetics, vanilloids, nitrous oxide inhibitors, anti-apoptotic agents, macrophage activation inhibitors, antimetabolites, neuroprotectants, calcium channel blockers, gamma-aminobutyric acid (GABA) antagonists, alpha agonists, anti-psychotic agents, tyrosine kinase inhibitors, nucleoside compounds, and nucleotide compounds, and analogs, derivatives, pharmaceutically acceptable salts, esters, prodrugs, codrugs, and protected forms thereof, and outflow increasing agents comprising ethacrynic acid or analogs and derivatives thereof, and combinations thereof.

3. The method according to claim 1, wherein the ophthalmic agent is administered with a viscoelastic agent.

4. The method according to claim 3, wherein the ratio of the ophthalmic agent to viscoelastic agent is 3:1.

5. A method of delivering an ophthalmic agent to the aqueous outflow system comprising: (a) placing an elastomeric material around the equator of an eye thereby occluding venous blood flow within the episcleral vein, wherein the elastomeric material comprises a planar body, and the body comprising: a central opening having an inner diameter and an outer diameter of at least 1 mm, wherein when the elastomeric material is configured to be placed upon the eye, the inner diameter portion is stretched to fit around the equator of the eye and, upon contraction, the venous blood flow within the episcleral vein of the eye is occluded; (b) administering to the episcleral vein an ophthalmic agent; and (c) removing the elastomeric material from the eye.

6. The method according to claim 5, wherein the ophthalmic agent is selected from the group consisting of steroids, alpha receptor agonists, beta receptor antagonists, carbonic anhydrase inhibitors, adrenergic agents, physiologically active peptides and/or proteins, antineoplastic agents, antibiotics, analgesics, anti-inflammatory agents, muscle relaxants, anti-epileptics, anti-ulcerative agents, anti-allergic agents, cardiotonics, anti-arrhythmic agents, vasodilators, antihypertensive agents, anti-diabetic agents, anti-hyperlipidemics, anticoagulants, hemolytic agents, antituberculous agents, hormones, narcotic antagonists, osteoclastic suppressants, osteogenic promoters, angiogenesis suppressors, antibacterials, non-steroidal anti-inflammatory drugs (NSAIDs), glucocorticoids or other anti-inflammatory corticosteroids, alkaloid analgesics, such as opioid analgesics, antivirals, such as nucleoside antivirals or a non-nucleoside antivirals, anti-benign prostatic hypertrophy (BPH) agents, anti-fungal compounds, antiproliferative compounds, anti-glaucoma compounds, immunomodulatory compounds, cell transport/mobility impeding agents, cytokines pegylated agents, alpha-blockers, anti-androgens, anti-cholinergic agents, purinergic agents, dopaminergic agents, local anesthetics, vanilloids, nitrous oxide inhibitors, anti-apoptotic agents, macrophage activation inhibitors, antimetabolites, neuroprotectants, calcium channel blockers, gamma-aminobutyric acid (GABA) antagonists, alpha agonists, anti-psychotic agents, tyrosine kinase inhibitors, nucleoside compounds, and nucleotide compounds, and analogs, derivatives, pharmaceutically acceptable salts, esters, prodrugs, codrugs, and protected forms thereof, and outflow increasing agents comprising ethacrynic acid or analogs and derivatives thereof, and combinations thereof.

7. The method according to claim 5, wherein the ophthalmic agent is administered with a viscoelastic agent.

8. The method according to claim 7, wherein the ratio of the ophthalmic agent to viscoelastic agent is 3:1.

9. A method of delivering an ophthalmic agent to the anterior chamber of an eye comprising: (a) placing an elastomeric material around the equator of the eye thereby occluding venous blood flow within the episcleral vein, wherein the elastomeric material comprises a planar body, and the body comprising: a central opening having an inner diameter and an outer diameter of at least 1 mm, wherein when the elastomeric material is configured to be placed upon the eye, the inner diameter portion is stretched to fit around the equator of the eye and, upon contraction, the venous blood flow within the episcleral vein of the eye is occluded; (b) administering to the episcleral vein an ophthalmic agent; and (c) removing the elastomeric material from the eye.

10. The method according to claim 9, wherein the ophthalmic agent is selected from the group consisting of steroids, alpha receptor agonists, beta receptor antagonists, carbonic anhydrase inhibitors, adrenergic agents, physiologically active peptides and/or proteins, antineoplastic agents, antibiotics, analgesics, anti-inflammatory agents, muscle relaxants, anti-epileptics, anti-ulcerative agents, anti-allergic agents, cardiotonics, anti-arrhythmic agents, vasodilators, antihypertensive agents, anti-diabetic agents, anti-hyperlipidemics, anticoagulants, hemolytic agents, antituberculous agents, hormones, narcotic antagonists, osteoclastic suppressants, osteogenic promoters, angiogenesis suppressors, antibacterials, non-steroidal anti-inflammatory drugs (NSAIDs), glucocorticoids or other anti-inflammatory corticosteroids, alkaloid analgesics, such as opioid analgesics, antivirals, such as nucleoside antivirals or a non-nucleoside antivirals, anti-benign prostatic hypertrophy (BPH) agents, anti-fungal compounds, antiproliferative compounds, anti-glaucoma compounds, immunomodulatory compounds, cell transport/mobility impeding agents, cytokines pegylated agents, alpha-blockers, anti-androgens, anti-cholinergic agents, purinergic agents, dopaminergic agents, local anesthetics, vanilloids, nitrous oxide inhibitors, anti-apoptotic agents, macrophage activation inhibitors, antimetabolites, neuroprotectants, calcium channel blockers, gamma-aminobutyric acid (GABA) antagonists, alpha agonists, anti-psychotic agents, tyrosine kinase inhibitors, nucleoside compounds, and nucleotide compounds, and analogs, derivatives, pharmaceutically acceptable salts, esters, prodrugs, codrugs, and protected forms thereof, and outflow increasing agents comprising ethacrynic acid or analogs and derivatives thereof, and combinations thereof.

11. The method according to claim 9, wherein the ophthalmic agent is administered with a viscoelastic agent.

12. The method according to claim 11, wherein the ratio of the ophthalmic agent to viscoelastic agent is 3:1.

13. A method of increasing intraocular pressure in a subject comprising:
   (a) placing an elastomeric material around the equator of the eye thereby occluding venous blood flow within the episcleral vein, wherein
      the elastomeric material comprises a planar body, and the body comprising: a central opening having an inner diameter and an outer diameter of at least 1 mm, wherein when the elastomeric material is configured to be placed upon the eye, the inner diameter portion is stretched to fit around the equator of the eye and, upon contraction, the venous blood flow within the episcleral vein of the eye is occluded;
   (b) administering to the episcleral vein an ophthalmic agent and a viscoelastic agent;
   (c) removing the elastomeric material from the eye.

14. The method according to claim 13, wherein the ophthalmic agent is selected from the group consisting of steroids, alpha receptor agonists, beta receptor antagonists, carbonic anhydrase inhibitors, adrenergic agents, physiologically active peptides and/or proteins, antineoplastic agents, antibiotics, analgesics, anti-inflammatory agents, muscle relaxants, anti-epileptics, anti-ulcerative agents, anti-allergic agents, cardiotonics, anti-arrhythmic agents, vasodilators, antihypertensive agents, anti-diabetic agents, anti-hyperlipidemics, anticoagulants, hemolytic agents, anti-tuberculous agents, hormones, narcotic antagonists, osteoclastic suppressants, osteogenic promoters, angiogenesis suppressors, antibacterials, non-steroidal anti-inflammatory drugs (NSAIDs), glucocorticoids or other anti-inflammatory corticosteroids, alkaloid analgesics, such as opioid analgesics, antivirals, such as nucleoside antivirals or a non-nucleoside antivirals, anti-benign prostatic hypertrophy (BPH) agents, anti-fungal compounds, antiproliferative compounds, anti-glaucoma compounds, immunomodulatory compounds, cell transport/mobility impeding agents, cytokines pegylated agents, alpha-blockers, anti-androgens, anticholinergic agents, purinergic agents, dopaminergic agents, local anesthetics, vanilloids, nitrous oxide inhibitors, anti-apoptotic agents, macrophage activation inhibitors, antimetabolites, neuroprotectants, calcium channel blockers, gamma-aminobutyric acid (GABA) antagonists, alpha agonists, anti-psychotic agents, tyrosine kinase inhibitors, nucleoside compounds, and nucleotide compounds, and analogs, derivatives, pharmaceutically acceptable salts, esters, prodrugs, codrugs, and protected forms thereof, and outflow increasing agents comprising ethacrynic acid or analogs and derivatives thereof, and combinations thereof.

15. The method according to claim 13, wherein the ratio of the ophthalmic agent to viscoelastic agent is 3:1.

16. The method according to claim 13, wherein the ophthalmic agent is administered concurrently with the viscoelastic agent.

17. The method according to claim 13, wherein the ophthalmic agent is administered before the viscoelastic agent.

18. The method according to claim 13, wherein the viscoelastic agent is administered before the ophthalmic agent.

* * * * *